US010852251B2

(12) United States Patent
Portune et al.

(10) Patent No.: US 10,852,251 B2
(45) Date of Patent: Dec. 1, 2020

(54) APPARATUS FOR CHEMICAL CONCENTRATION DETERMINATION USING MICROWAVE SPECTROSCOPY

(71) Applicant: Nokomis, INC., Charleroi, PA (US)

(72) Inventors: Andrew Richard Portune, Oakdale, PA (US); Walter John Keller, Bridgeville, PA (US); Todd Eric Chornenky, Carmichaels, PA (US)

(73) Assignee: NOKOMIS, INC., Charleroi, PA (US)

( * ) Notice: Subject to any disclaimer, the term of this patent is extended or adjusted under 35 U.S.C. 154(b) by 921 days.

(21) Appl. No.: 14/922,616

(22) Filed: Oct. 26, 2015

(65) Prior Publication Data

US 2016/0116422 A1  Apr. 28, 2016

Related U.S. Application Data

(60) Provisional application No. 62/122,590, filed on Oct. 24, 2014.

(51) Int. Cl.
*G01N 22/00* (2006.01)
*G01N 33/36* (2006.01)
*G07D 7/10* (2006.01)

(52) U.S. Cl.
CPC ........... *G01N 22/00* (2013.01); *G01N 33/367* (2013.01); *G07D 7/10* (2013.01)

(58) Field of Classification Search
CPC ...... G01N 22/04; G01N 22/00; G01N 33/367; G01N 33/36; G07D 7/10
See application file for complete search history.

(56) References Cited

U.S. PATENT DOCUMENTS

| 4,484,133 | A | * | 11/1984 | Riggin | ................... | G01N 22/04 324/606 |
| 5,124,653 | A | * | 6/1992 | Andresen | ............... | G01N 22/00 324/633 |
| 9,551,686 | B1 | * | 1/2017 | Griffith | ................... | G01N 22/00 |
| 2001/0019271 | A1 | * | 9/2001 | Scott | ...................... | G01N 22/00 324/637 |
| 2003/0032000 | A1 | * | 2/2003 | Liu | ........................ | G01N 22/00 435/4 |
| 2006/0028213 | A1 | * | 2/2006 | Typpo | .................. | D21G 9/0027 324/640 |
| 2007/0159175 | A1 | * | 7/2007 | Prins | .................. | G01N 15/0656 324/322 |
| 2009/0064276 | A1 | * | 3/2009 | Dugas | .............. | G01N 35/00732 726/2 |

(Continued)

*Primary Examiner* — Son T Le
*Assistant Examiner* — Dustin R Dickinson
(74) *Attorney, Agent, or Firm* — AP PATENTS

(57) ABSTRACT

Compound detection or testing apparatus includes a microwave power supply, an antenna electrically coupled to the microwave power supply, the antenna adapted to emit energy during use of the apparatus, the antenna further adapted to receive an unabsorbed energy from the material and generate a signal defining the unabsorbed energy, a processing components configured to process the signal and determine a concentration of the compound on/in the fabric material and a reporting member coupled to each of the power supply and the processing member the reporting component configured to communicate the concentration of the compound on/in the fabric material. The apparatus may be configured as a hand-held sensor.

24 Claims, 5 Drawing Sheets

(56) References Cited

U.S. PATENT DOCUMENTS

| | | | |
|---|---|---|---|
| 2011/0293553 A1* | 12/2011 | Wu | A01N 25/00 |
| | | | 424/84 |
| 2012/0223221 A1* | 9/2012 | Jones | B82Y 15/00 |
| | | | 250/269.1 |
| 2013/0154668 A1* | 6/2013 | Leflour | G01N 22/02 |
| | | | 324/637 |

* cited by examiner

APPARATUS FOR CHEMICAL CONCENTRATION DETERMINATION USING MICROWAVE SPECTROSCOPY

CROSS-REFERENCE TO RELATED APPLICATIONS

This application is related to and claims priority from U.S. Provisional Patent Application Ser. No. 62/122,590 filed on Oct. 24, 2014.

STATEMENT REGARDING FEDERALLY SPONSORED RESEARCH AND DEVELOPMENT

N/A

REFERENCE TO SEQUENCE LISTING, A TABLE, OR A COMPUTER PROGRAM LISTING COMPACT DISC APPENDIX

N/A

BACKGROUND

1. Technical Field

The subject matter relates to measurement of chemical concentration. It further relates to an apparatus for chemical concentration measurements that employs microwave spectroscopy. The subject matter additionally relates to an apparatus that employs transmit and receive antennas and that is configured to simultaneously detect and quantify the concentration of chemical constituents within a solid, liquid, or gaseous medium for one or more chemical species.

2. Description of Related Art

As is generally known, the concentration of chemicals in a gaseous, liquid, or solid medium controls the macroscopic properties of the substance. As an example, permethrin concentration in clothing used by civilians and military personnel may be responsible for the article's effectiveness in deterring, disabling, and killing biting insects. Permethrin content in the uniforms and clothing decreases as a user performs active duty in the field, increasing exposure to disease-carrying biting insects in high-risk operational areas around the globe.

Uniforms and standard civilian clothing intended for outdoors activities are conventionally treated with permethrin to protect against vector-borne diseases that pose significant health threats to many, particularly, those deployed users around the globe. Permethrin is a chlorinated pyrethrin that has been used for insect and insecticide applications for over 40 years. While non-toxic to humans, permethrin is an extremely effective neurotoxin against biting insects, providing an ideal Personal Protective Measure (PPM) against diseases carried by such pests. Low concentrations of permethrin ($<0.10$ mg/cm$^2$) have proved an effective deterrent.

Uniforms used by defense personnel may be initially treated with 0.104-0.170 mg/cm$^2$ depending on uniform location. While permethrin concentration fading is understood for laundering cycles, it is currently impossible to measure how permethrin fades when uniforms are used in the field. Currently, destructive chemical tests are used to determine permethrin concentration in laboratory settings. Samples are cut from treated uniforms after which the permethrin is extracted by a solvent and measured using a Gas Chromatography-Mass Spectrometer (GCMS). Testing requires at least two technicians and nine (9) man-hours. This test method cannot be transferred for field use due to the time required for testing, the complexity of test equipment, and the use of chemical solvents.

Current best practices for detecting permethrin are costly in both time and resources, requiring access to laboratory equipment that cannot be brought on field missions. Field-testing is needed to verify that uniforms provide the necessary protection to ensure mission success. Therefore, there is a need for a non destructive method for determining concertation of the permethrin. There is a further need for a portable non-destructive permethrin test device capable of performing in-situ measurements to verify the protectiveness of the uniforms and treated articles of clothing in the field.

BRIEF DESCRIPTION OF THE DRAWINGS

The accompanying drawings are incorporated in and constitute part of the specification and illustrate various embodiments. In the drawings.

DETAILED DESCRIPTION OF EXEMPLARY EMBODIMENTS

Figure 1:
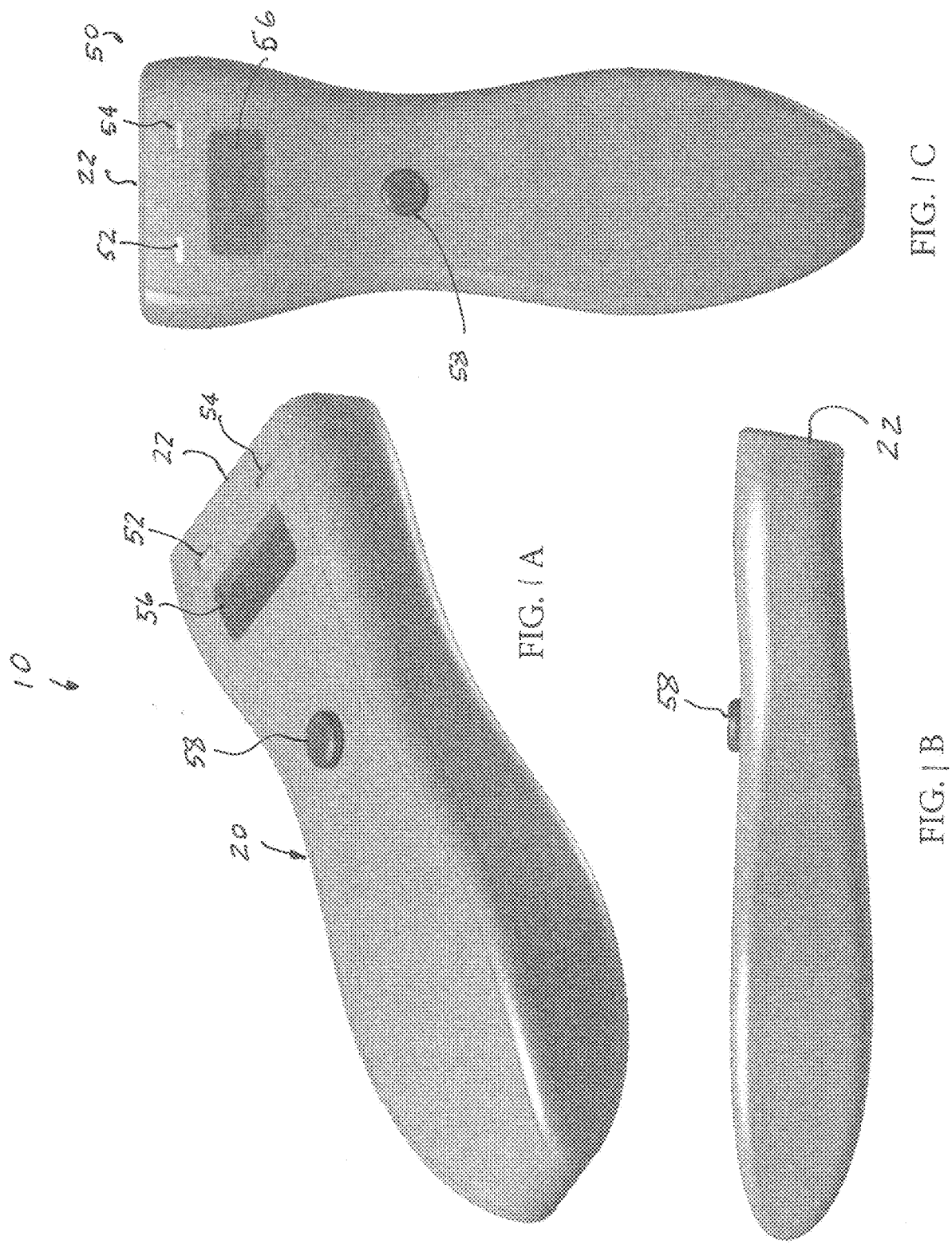
FIG. 1A illustrates an apparatus of one exemplary embodiment configured as a hand-held device to detect a presence and/or a concentration of a chemical compound.
FIG. 1B is a front view of the apparatus of FIG. 1A.
FIG. 1C is a top view of the apparatus of FIG. 1A.

Prior to proceeding to the more detailed description of the present invention, it should be noted that, for the sake of clarity and understanding, identical components which have identical functions have been identified with identical reference numerals throughout the several views illustrated in the drawing figures.

The following detailed description is merely exemplary in nature and is not intended to limit the described examples or the application and uses of the described examples. As used herein, the words "example", "exemplary" or "illustrative" means "serving as an example, instance, or illustration." Any implementation described herein as "example", "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," "exterior," "interior," and derivatives thereof shall relate to the invention as oriented in the Figures. Furthermore, there is no intention to be bound by any expressed or implied theory presented in the preceding technical field, background, or the following detailed description. It is also to be understood that the specific devices and processes illustrated in the attached drawings, and described in the following specification, are simply examples of the inventive concepts defined in the appended claims. Hence, specific dimensions and other physical characteristics relating to the examples disclosed herein are not to be considered as limiting, unless the claims expressly state otherwise.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

In one exemplary embodiment, the subject matter provides apparatus and method for determining a presence and/or a concentration of a chemical compound. Compound may comprise one or more chemical species. All chemical species absorb microwave radiation at characteristic frequencies where energy transitions occur, such as molecular rotations, translations, and dipole moment transitions.

The particular embodiments employ a microwave inspection. In these particular embodiments, inspection time is nearly instantaneous, equipment has low Size, Weight, and Power (SWaP) requirements, and testing is entirely non-destructive and non-hazardous to deployed military personnel and their uniforms.

In particular embodiments, the subject matter utilizes an ultra-sensitive microwave sensor 10 (apparatus) for the detection and determination of the concentration of permethrin in military uniforms and civilian clothing typically in a rapid (<2 seconds) test. The sensor 10 can take a form of a handheld device, a benchtop apparatus or a stationary apparatus. When the sensor 10 is configured as the handheld apparatus, it can be constructed to weigh less than two (2) pounds with a volume under eleven (<10.8) cubic inches. The sensor 10 may comprise a conformal antenna 26 on the front of the housing 20 of the sensor 10 that is placed in a direct contact with or close to the article of clothing to be tested at any location of interest. The compound concentration and/or presence may be determined and displayed on an easily read screen with a single button push. All calculations of the compound presence and concentration can be performed automatically through embedded software and firmware assets such that minimal to no training is required for successful sensor 10 operation.

The particular embodiments provide a rapid, non-destructive, in-situ test technique, to enable determination of suitable permethrin content in the field to verify that military personnel are suitably protected from disease-carrying insects.

The particular embodiments provide an apparatus that is configured to measure permethrin concentration under field conditions in a rapid (near-instantaneous) manner any location of the uniform or treated article of clothing.

The particular embodiments provide a permethrin processing apparatus that compensates for environmental conditions (humidity, precipitation, temperature, etc.).

The particular embodiments provide a permethrin concertation test method that is non-destructive to fabric material.

The particular embodiments provide a permethrin concertation test method that is non-hazardous to personnel tasked with performing the test.

The particular embodiments provide a permethrin concertation test method that does not require training of personnel tasked with performing the test, beyond simple steps of turning a test apparatus on, positioning one end of the device on or in a proximity to the fabric material, activating the test apparatus and reading the displayed results.

The particular embodiments provide a permethrin concertation test method that does not use solvents during testing.

The particular embodiments provide a permethrin concertation test method and/or apparatus that detect low permethrin concentrations.

The particular embodiments provide a permethrin concertation test method and/or apparatus that do not require a fabric material sample to be separated/removed from the article of clothing.

Figure 3:
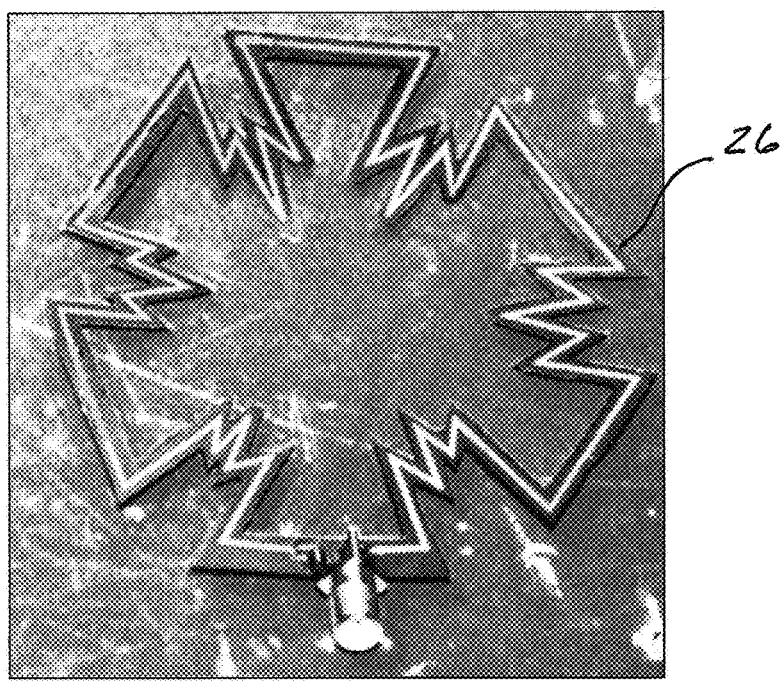
FIG. 3 illustrates an example of an antenna layout that can be employed in apparatus of FIGS. 1A-2.

In an exemplary embodiment of FIGS. 1A. 1B, 1C and 2, the sensor 10 (compound detection apparatus) comprises a housing 20 defining a hollow interior and one end thereof being configured for positioning adjacent or on a surface of the chemical compound 2. Such one end includes a face plate 22. A power supply 24, for example such as DC power supply, is disposed within the hollow interior. An antenna 26 (probe) may be disposed within the hollow interior adjacent the one end of the housing 20. The antenna 26 may be imbedded into the face plate 22. The antenna 26 is adapted to generate and emit electromagnetic energy (radiation) during use of the sensor 10. The antenna 26 can be further adapted to receive an unabsorbed energy from the chemical specie and generate a signal defining the unabsorbed energy. The antenna 26 may be one of a horn antenna, a near field antenna and a conformal antenna. Conformal antenna 26 may be of an example of FIG. 3. The antenna 26 is configured to emit the electromagnetic energy at frequencies of at least one of RF radiation, microwave radiation, millimeter-wave radiation, Terahertz wave radiation, infrared radiation, visible light radiation ultraviolet radiation and x-ray radiation. The antenna 26 may be configured to emit electromagnetic energy at pre-chosen frequencies within a range of about 30 Mhz to about 300 Ghz, corresponding to absorption frequencies associated with the chemical specie. When the antenna 26 is further configured to receive energy, such energy can be detected at frequencies of at least one of RF radiation, microwave radiation, millimeter-wave radiation, Terahertz wave radiation, infrared radiation, visible light radiation ultraviolet radiation and x-ray radiation.

Figure 2:
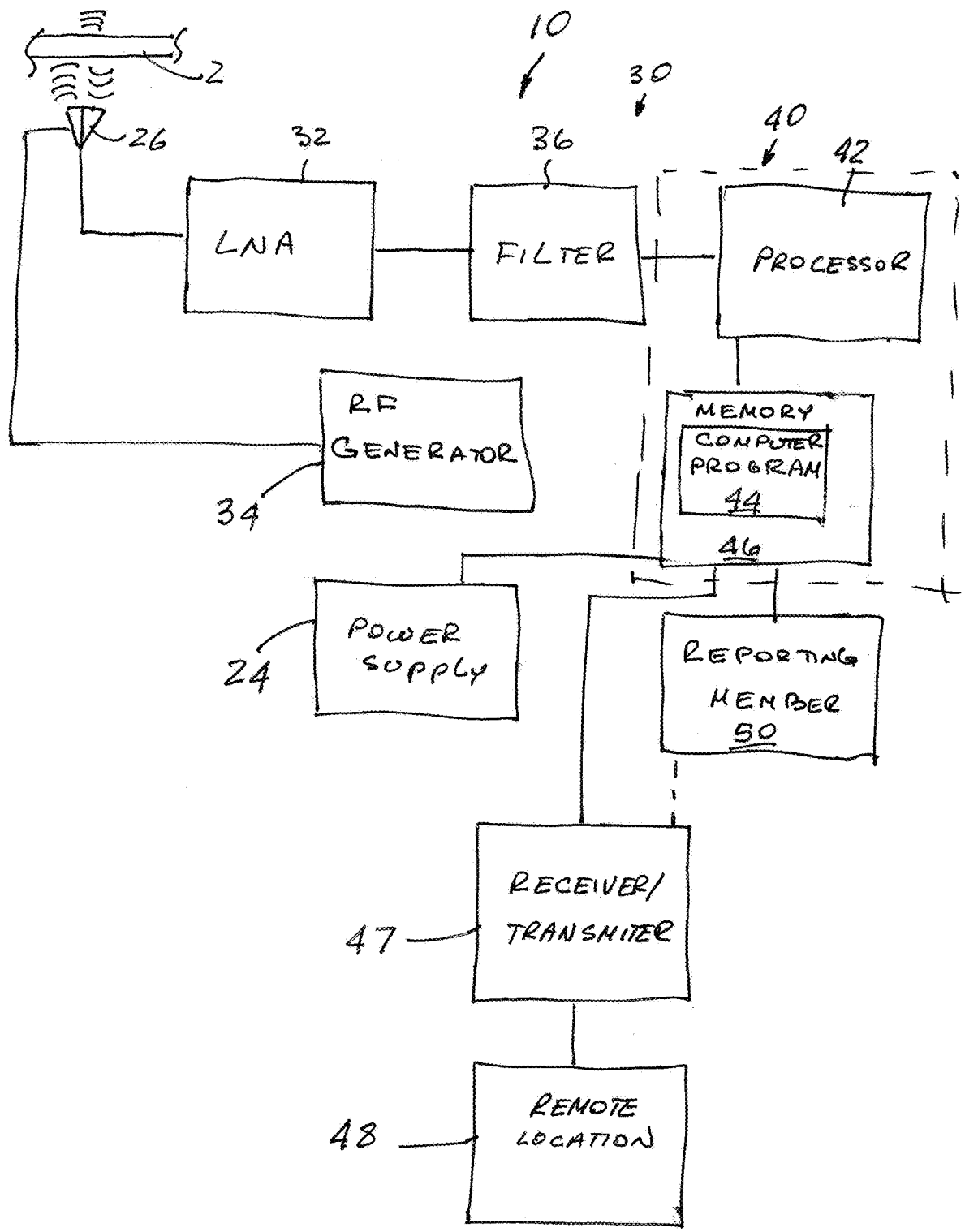
FIG. 2 illustrates a bloc diagram of an apparatus configured to detect presence and/or concentration of a chemical compound.

There is also a signal processing member 30 that is coupled to the antenna 26 and may be further coupled to the power supply 24, the signal processing member 30 configured to process the signal and determine a concentration of the chemical specie. The signal processing member 30 may be disposed within the hollow interior of the housing 20 or may be disposed remotely, for example in a remote location of FIG. 2, and coupled to the antenna 26 in one of a wireless and wired coupling connections. The signal processing member 30 is configured to process the signal defining the unabsorbed energy and characterize the chemical specie and/or concentration of such chemical specie in an external host, for example such as a fabric material. The signal processing member 30 may be referred to as an electromagnetic receiver that translates electromagnetic energy frequencies received and their corresponding energy levels into at least one of digital or analog translated representations. The signal processing member 30 may comprise a Low Noise Amplifier (LNA) 32 coupled to the antenna 26 and operable to increase power level of the signal therefrom. The signal processing member 30 may further comprise a hardware or software RF signal generator and tuner 34, coupled to the antenna 26, to tune the transmitted energy to predesignated absorption frequencies associated with the chemical specie and tune the receiver to a corresponding frequency indicated by the chemical specie response. The RF signal generator 34 may be a microwave power source or radiofrequency (RF) power generator. The signal processing member 30 may comprise a single or a set of hardware or software bandpass or band reject filters or tuner 36 tuned to the specifically predesignated absorption frequencies associated with the chemical specie. Such filter(s) 36 when provided is connected to an output from LNA and is further connected to an input of the processing member 40. The processing member 40 may be a computer. The processing member 40 may comprise one or more processors 42 and non-transitory tangible computer readable medium and/or tangible computational medium 44 comprising algorithms and/or executable instructions (computer program code), that cause the one or more processors to process the signal defining the unabsorbed energy. The non-transitory tangible computer readable medium and/or tangible computational medium 44 may be a computer program. There is also a non-transitory storage medium (memory) 46 that stores such computer program.

Tangible computer readable medium means any physical object or computer element that can store and/or execute computer instructions. Examples of tangible computer readable medium include, but not limited to, a compact disc (CD), digital versatile disc (DVD), blu-ray disc (BD), usb floppy drive, floppy disk, random access memory (RAM), read-only memory (ROM), erasable programmable read-only memory (EPROM), optical fiber, etc. It should be noted that the tangible computer readable medium may even be paper or other suitable medium in which the instructions can be electronically captured, such as optical scanning. Where optical scanning occurs, the instructions may be compiled, interpreted, or otherwise processed in a suitable manner, if necessary, and then stored in computer memory.

Alternatively, it may be a plugin or part of a software code that can be included in, or downloaded and installed into a computer application. As a plugin, it may be embeddable in any kind of computer document, such as a webpage, word document, pdf file, mp3 file, etc.

In any form, the signal processing member 30 is configured to transform raw energy received at the antenna 26 or at a receiving element into an electrical signal that can be processed and analyzed. Or antenna 26 may be configured to transform the raw energy into the electrical signal with the signal processing member 30 being then configured to process such signal.

A reporting member 50 may be provided in a coupling connection with each of the microwave power generator 34 and the signal processing member 30, the reporting member 50 being configured to communicate the concentration of the chemical specie. The reporting member 50 may be configured to generate at least one of visual, audio, and tactile signaling elements indicating, for example, a threshold degree of the chemical specie concentration in a fabric material.

The sensor 10 may be configured as a benchtop apparatus or a fixed apparatus. The apparatus may be configured as a hand-held apparatus, for example as is illustrated in FIGS. 1A, 1B and 1C, where the housing 20 is shaped and sized to be grasped by a hand of a person tasked with detecting concentration of the chemical specie. When the sensor 10 is configured as a hand-held apparatus, the signal processing member 30 is disposed within the hollow interior and the reporting member 50 may be defined by a pair of visual annunciators, for example such as light emitting diodes (LED) 52, 54 and a display 56, all viewable from the exterior surface of the housing 20.

When the sensor 10 is configured as a hand-held apparatus, size, weight and Power (SWaP) specifications for the apparatus may be of an example in Table 1. As has been described above, signal acquisition is performed via the conformal antenna 26 that may be positioned in the front/face plate 22 of the device. Signal processing is performed using a System-in-a-Package (SiP) that includes programmable logic and dedicated microwave hardware assets (e.g. Low Noise Amplifier (LNA), Analog to Digital Converter (ADC), etc.), which have been selected to maximize sensitivity. The SiP may be configured to consume little power, enabling the apparatus to have a reasonable battery life (>4 hrs of active use) while remaining within SWaP constraints.

TABLE 1

Exemplary specifications for the handheld chemical specie detection device

| | Specification |
|---|---|
| Dimensions | 6.0" × 1.8" × 1" (L × W × H) |
| Weight | <2 lbs. |
| Power | <10 W |
| Connections | Ethernet, USB (recharging/software updates) |
| Permethrin Sensitivity | <0.001 mg/cm$^2$ |
| User Notifications | Visual (display screen and LED) |

Microwave absorption by chemical species can manifest itself in that molecules preferentially absorb microwave energy at frequencies where atomic or molecular energy state transitions occur. Such transitions include dipolar polarization, ionic conduction, molecular rotation, and molecular translation. The ability of a specific material or chemical specie to absorb energy at a particular frequency may be generally represented by its loss tangent delta (tan δ). The loss tangent is a highly frequency dependent, with large values indicating strong absorption at that particular frequency. Exemplary loss tangent values at 2.45 GHz for various polar and nonpolar chemicals is shown in Table 2.

TABLE 2

Loss tangents (tan δ) of selected solvents at 2.45 GHz

| Solvent | tan δ | Solvent | tan δ |
|---|---|---|---|
| Ethylene glycol | 1.350 | 1,2-Dichloroethane | 0.127 |
| Ethanol | 0.941 | Water | 0.123 |
| DMSO | 0.825 | Chloroform | 0.091 |
| Methanol | 0.659 | Acetonitrile | 0.062 |
| 1,2-Dichlorobenzene | 0.280 | Tetrahydrofuran | 0.047 |
| NMP | 0.275 | Dichloromethane | 0.042 |
| Acetic Acid | 0.174 | Toluene | 0.040 |
| DMF | 0.161 | Hexane | 0.020 |

Thus, in one embodiment, the antenna 26 is operable, with sufficiently broad frequency response, to sweep the compound 2 with different (incremental) frequencies in a specific range or specific ranges and the signal processing member 30 is then configured through hardware and/or software (programmed) to calculate loss tan δ or a similar indicator based on the attenuated energy at each frequency and identify frequency or frequencies at which the energy state transition(s) occur(s).

Figure 4:
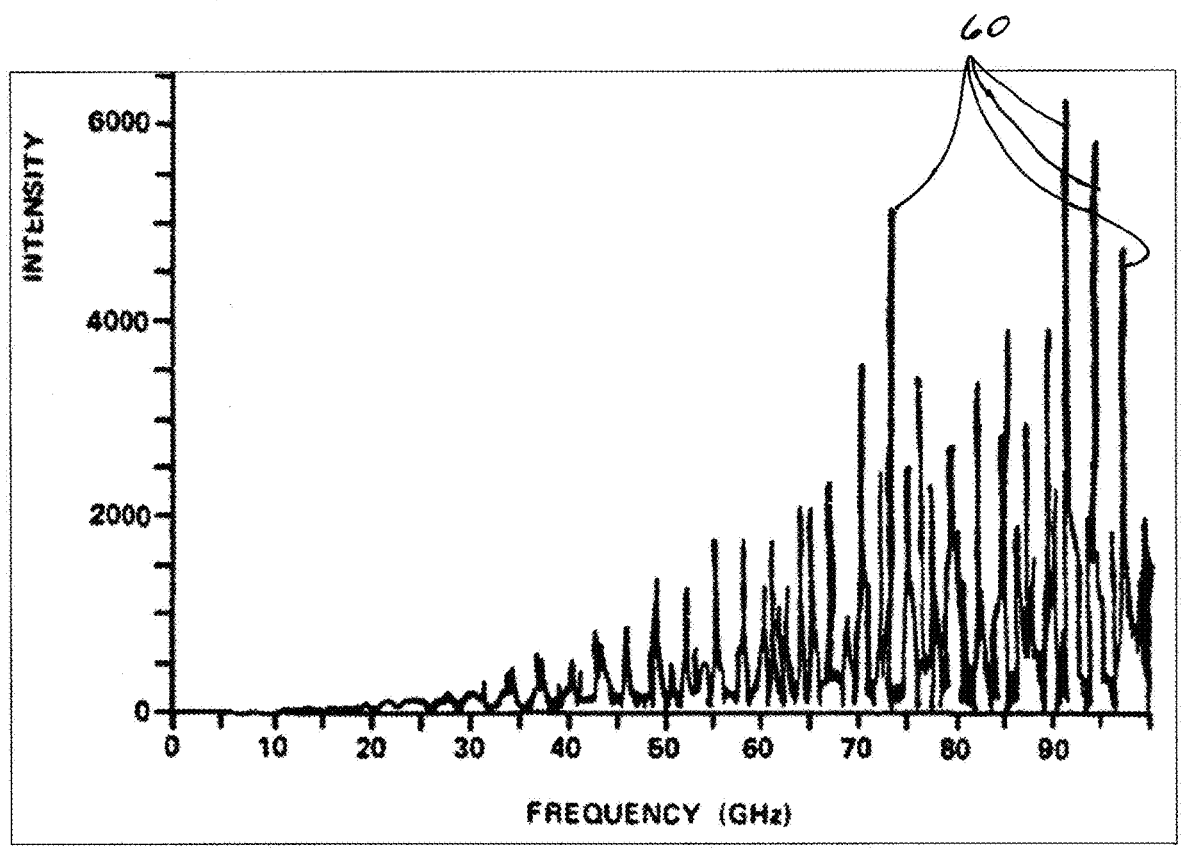
FIG. 4 illustrates exemplary microwave absorption spectrum of $[(CH_3)_2CHO]CH_3P(O)F$.

Since chemical compounds (species) may experience multiple energy state transitions within the microwave range as a function of frequency, the apparatus 10 can be configured to process and store energy state transition at each frequency increment within one or more ranges. Measurement and/or identification, by the signal processing member 30, of one or more frequencies of interest enables the detection of the chemical specie as well as enables an accurate measure of its concentration. Further, the microwave absorption spectrum is contemplated herewithin as a fingerprint or a signature due to its characteristic and unique relationship to the chemical compound. The exemplary spectrum of the nonpolar organophosphorous compound [(CH$_3$)$_2$CHO]CH$_3$P(O)F, containing frequency peaks 60, is shown in FIG. 4. It must be noted that the spectrum comprises many characteristic frequencies at which the chemical specie can be detected through the above technique/method. Thus, the method may require exploiting multiple characteristic frequencies of detection and/or characterization of the chemical specie.

In one exemplary embodiment, such chemical compound or specie 2 may be a permethrin on/in fabric material, as a carrying medium. Fabric material may be of the type as used in military uniforms and/or civilian clothing. In this exemplary embodiment, the apparatus and/or method are/is then configured to detect a concentration and/or a presence of Permethrin on/in fabric material. The microwave absorption and reemission spectrum for permethrin can be similar to that of nonpolar organophosphorous compound [(CH$_3$)$_2$CHO]CH$_3$P(O)F, especially since it shares many structural commonalities with this and other non-polar molecules.

Figure 5:
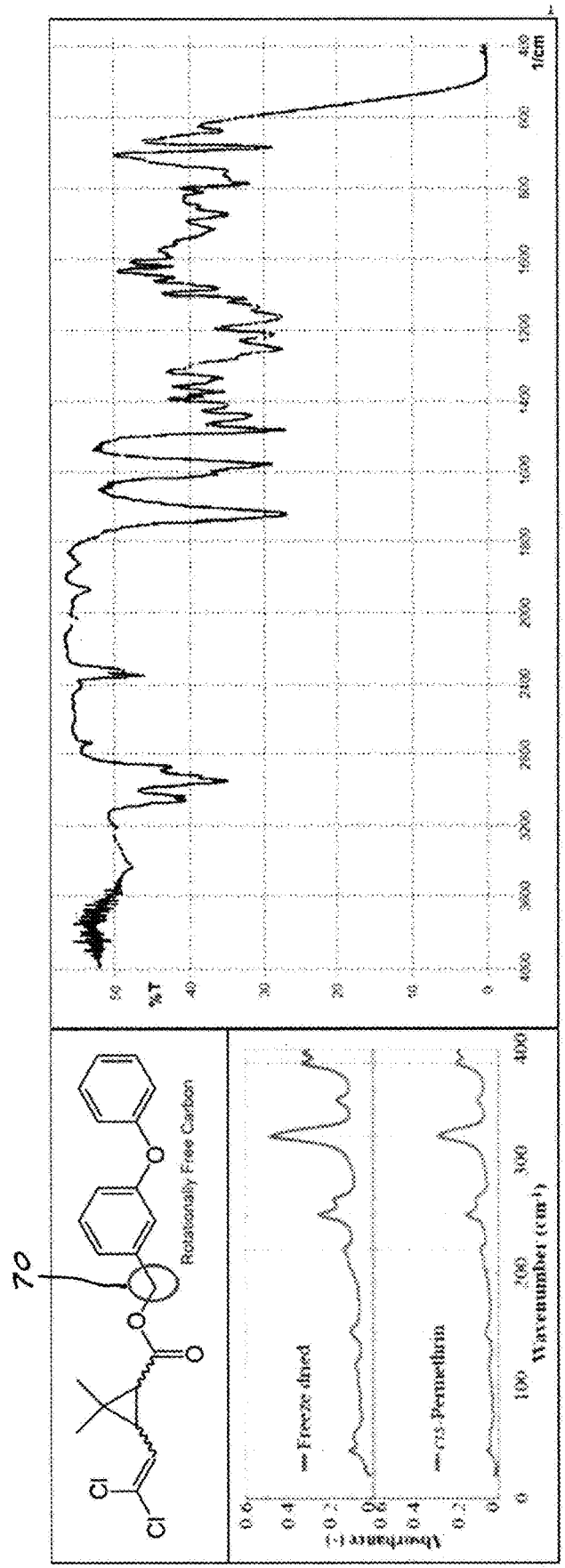
FIG. 5A illustrates permethrin molecule, with particular focus on the covalent bond which is free to rotate, and will rotate when exposed to microwave frequencies.
FIG. 5B illustrates permethrin's microwave power absorption amount versus frequency curves.
FIG. 5C is an enlarged view of FIG. 5B.

Now in a reference to FIG. 5A, permethrin's rotationally free carbon 70 is responsible for absorption phenomenology in the GHz microwave frequency range. Permethrin experiences multiple energy state transitions upon absorption of electromagnetic (EM) energy across a wide frequency band, from the infrared (IR) to below THz frequencies. Exemplary absorption spectra for permethrin are shown in FIGS. 5B and 5C. Based on these characteristic spectra, permethrin can be detected through microwave absorption by examining energy loss at key characteristic frequencies. Furthermore, specific frequency responses in the loss spectra can be constant despite the R/S or cis/trans aspects of permethrin's isomers as the rotationally free carbon responsible for absorption would remain constant between these isomers. This may be advantageous in application(s) targeting a racemic mixture used in treating the uniform or article of clothing. A racemic mixture is similarly common in products intended for civilian use.

The subject matter takes advantage of a condition wherein permethrin bonding to cellulosic and polyester fibers through weak van Der Waals forces leaves its covalent backbone susceptible to microwave excitation, enabling measurements on articles of treated clothing without requiring samples to be destructively prepared. Further, permethrin's constant emission into the atmosphere (Vapor pressure: $2.15 \times 10^{-8}$ mmHg) results in the local fabric material environment having a certain concentration of permethrin in the gaseous state, which could be further enhanced by microwave stimulation. Both of these aspects enhance microwave absorption measurements of a rotational microwave spectroscopy, which is typically conducted in a gaseous environment and relies upon exciting bonds with microwave energy.

Similar to the absorption spectrum shown in FIG. 4, permethrin's spectrum exhibits multiple characteristic absorption lines across multiple microwave bands ($K_u$ through F bands). The disclosed method improves detection statistics and the accuracy of quantitative permethrin concentration determination by measuring absorption of microwave bands at multiple frequencies. The disclosed method further improves detection of permethrin by tuning the antenna 26 to the next permethrin absorption line when interferes (e.g. sweat, blood, mud), that result in strong absorptions of microwave radiation or energy, have been present at a specific permethrin absorption line.

Absorption of microwave radiation may follow the Beer-Lambert relationship of Equation 1:

$$I = I_o e^{-\gamma x} \qquad \text{Equation 1:}$$

Where:
γ is the absorption coefficient (frequency dependent),
$I_o$ is the original signal intensity, and
x is the path length.

The absorption coefficient may be given by the Van Vleck-Weisskopf equation 2:

$$\gamma = \frac{8\pi^2 Nf}{3CkT}(u_{ij})^2 v^2 \frac{\Delta v}{(v-v_o)^2 + (\Delta v)^2} \qquad \text{Equation 2}$$

Where N is the number of molecules per millimeter,
$u_{ij}$ is the dipole matrix element connecting the upper and lower energy states, and
v is the energy state transition frequency.

The absorption coefficient is therefore linearly dependent on the number of chemical molecules present. Since the absorption coefficient is in the exponent of the Beer-Lambert equation, the relationship between chemical concentration and absorbed microwave energy will appear linear when absorption is measured on a logarithmic scale (e.g. frequency in GHz vs. absorption loss in dB).

Permethrin concentration was directly correlated with microwave test results based on the quantity of energy absorbed by the test sample. Based on the absorption behavior of other chemical species, including both polar and nonpolar species, the relationship between absorbed microwave energy and permethrin concentration was linear when microwave absorption is measured on a logarithmic scale (i.e. in dB). Measurement results for prepared test samples were analyzed to identify the relationship between concentration and absorbed energy. Functional parameters (e.g. slope and intercept should the relationship prove linear) of this relationship were determined through regression analysis.

In a further reference to FIGS. 1A, 1B 1C and 2, the exemplary sensor 10 (apparatus) for detecting a presence and/or a concentration of permethrin is a portable, handheld permethrin detection device for performing chemical detection and concentration measurements under field conditions. Antenna 26 as a microwave probe is used to introduce low-power microwaves into the uniform. The antenna 26 is embedded into the face plate 22 of the handheld sensor 10. The face plate 22 can be positioned in a direct contact with the fabric material or may be disposed at an incremental distance therefrom, for example anywhere from about 0.03 inches to about 3.0 inches. The antenna 26 can be designed to emphasize gain at frequencies at which permethrin undergoes energy state transitions to maximize sensitivity to minute chemical concentrations. The antenna 26 can be the conformal loop antenna 26 with maximum sensitivity around permethrin's microwave resonance frequencies. The antenna 26 can be manufactured using standard photolithography techniques with polyimide as a substrate material. The flexibility of polyimide enables the antenna 26 to conform to most surfaces on any treated article of clothing, enabling testing of permethrin at multiple locations. The antenna 26 is operable to emit electromagnetic energy (radiation) at pre-chosen frequencies in a range that may be within about 30 Mhz to about 300 Ghz range, corresponding to absorption frequencies associated with the compound 2.

The apparatus 10 may be adapted with a user-operable switch 58 to initiate permethrin testing, by simply connecting microwave or RF power to the antenna 26 and signal processing member 30. The switch 58 may be anyone of pushbutton, sliding, and tactile types. The signal processing member 30 may be also configured, through hardware and software, to operate antenna 26 at incremental frequencies within a specific frequency range so as to sweep the fabric material at different frequencies. In this example, the sensor (apparatus) 10 is configured as an automatic apparatus, where no user actions are required during sensing and measurement steps after activation of the apparatus.

The processing member 40 (within the signal processing member 30) can be configured and operable to define acquired absorption spectra resulting in energy loss by a broad curve of loss versus frequencies. The processing member 40 can execute multivariate curve resolution methods to recover concentration profiles represented in an acquired underlying microwave spectral features. The processing member 40 can utilize evolving factor analysis to recover concentration profiles represented in the acquired underlying microwave spectral features. The processing member 40 can utilize constraint propagation to recover concentration profiles representing the acquired underlying microwave spectral features.

The reporting member 50 can be provided as a simple display screen 56 with test results being displayed in real time on the display screen, including the concentration of permethrin and the Remaining Useful Life (RUL) of the article of clothing based on minimum concentration specifications and expected half-life in the clothing and usage environment. The display screen 56 can be of any type and can be further of a tactile type and can additionally incorporate the function of the switch 58. The reporting member 50 may be further provided as comprising red and/or green LEDs 52, 54. Red LED 52 may be employed and operated to flash or lit solid if no presence of permethrin is detected or the concentration is below specifications, based on the values stored in memory 46. Green LED 54 may be employed and operated to flash or lit solid if the detected permethrin concentration is within specifications. Green and red colors may be replaced by other colors. The reporting member 50 can be further provided as an output coupled to the processing member 40, for example through an optional wireless transmitter or connector to a remote location 48, containing such processing member 40 or any other processing member. Such remote location 48 may be a stand-alone computer, a network computer or a server that catalogs (stores in memory) all test measurements for future use or actions. For example, the stored values can be analyzed so as to determine the initial concentration (amount) of permethrin to be applied onto a brand new article of clothing, reapplied after washing or reapplied during filed actions. The stored value can be also used to determine a time increment for reapplying permethrin. The resulting decision can be communicated from the remote location 48 to an optional wireless receiver disposed within the housing 20 or the transmitter and receiver can be provided as a transceiver 47. If the processing member 48 is disposed remotely from the housing 20, the sensor 10 can be configured to simply transmit the signal from the antenna 26 and display results on the display 56 and/or operates the LEDs 52 and 54.

The reporting member 50 can be configured to generate at least one of visual, audio, and tactile signaling elements indicating a threshold degree of the compound concentration in the fabric material. The reporting member 50 can report a threshold of level of absorption of one or more absorption frequencies of the chemical specie based on matching to levels represented in a predesignated mask of absorption frequencies for the chemical specie, as determined by the processing member.

One exemplary method for determining a presence and/or concentration of a compound 2 comprises sweeping, using an antenna 26 (illumination element), the compound 2 with an electromagnetic energy in a range of frequencies, measuring, with a signal processing member 30, scattering parameters at each frequency within the range of frequencies, and determining, with the signal processing member 30 (analysis element), based on the scattering parameters, the concentration of the compound 2. In an example, measuring of scattering parameters may comprise generating a curve based on an absorption coefficient of the compound 2. In an example, measuring of scattering parameters may comprise selecting frequencies at which, upon absorption thereof, the compound 2 undergoes state changes. In an example, measuring of scattering parameters may comprise constructing a curve based on frequency peaks. In an example, measuring of scattering parameters may comprise comparing phases at each frequency. In an example, measuring of scattering parameters may comprise comparing phases between at least two frequencies.

In an exemplary embodiment, a compound detection apparatus 80 comprises an illumination element 82 being at least one of RF, microwave and millimeter wave illumination transmission type, configured and operable to illuminate, with electromagnetic energy, a compound 2 under a test and/or a detection; a receiver element 85 configured to receive spectra of the electromagnetic energy that is transmitted through a medium that contains the compound 2 under the test and/or the detection; a receiver element 84 configured to receive spectra of electromagnetic energy that is reflected from the medium that contains the compound 2 under the test and/or the detection; a measurement element 86 that is connected to at least one of the receiver element configured to receive the spectra of electromagnetic energy that is reflected from the medium and the receiver element configured to receive the spectra of electromagnetic energy that is reflected from the medium, the measurement element configured to determine a value or amount of reflected electromagnetic energy and/or absorbed electromagnetic energy; and an analysis element 88 that analyzes information collected by the measurement element and defines chemical specie(s) within the compound 2. The illumination element 82 may be the above described antenna 26 and the measurement element 86 and the analysis element 88 may be configured and function as the above described signal processing member 30. The apparatus 80 may further include the above described reporting member 50 or any other reporting member sufficient to report test results, for example such as presence and/or concentration of the compound 2.

The illumination element 82 may be operable to transmit the electromagnetic energy (radiation) at least one frequency. The illumination element 82 can be operable to transmit the electromagnetic energy at least one frequency being in a range from about 1 MHz to 1 about GHz, in a range from about 1 GHZ to about 10 GHZ; in a range from about 10 GHz to about 100 GHz and in a range from about 100 GHz to about 300 GHz. The illumination element 82 can be operable to transmit one or more frequency in each of a frequency range from about 1 MHz to about 1 GHz, a frequency range from about 1 GHZ to about 10 GHZ, a frequency range from about 10 GHz to about 100 GHz and a frequency range from about 100 GHz to about 300 GHz is utilized simultaneously to differentiate the chemical makeup of the compound 2 The illumination element 82 can be operable to transmit the electromagnetic energy at one or more frequencies and wherein at least one of the one or more frequencies is modulated to determine chemical composition of the compound 2. The analysis element 88 can be configured to compare phases of at least one of the reflected and transmitted electromagnetic energy. The analysis element 88 can be configured to compare phases of at least two frequencies. The analysis element 88 can be configured to compare phases of at least one of the reflected and transmitted electromagnetic energy over at least two different frequencies. The absorption spectra in the compound 2 may result in the electromagnetic energy loss at at least two characteristic frequencies. The measurement element 86 may comprise a hardware or software tuner to tune the illumination element to specifically predesignated absorption frequencies associated with the compound. The measurement element 86 may comprise algorithms to reactively at least one of tune to specifically predesignated absorption frequencies and provide a specific frequency and/or amplitude modulation parameter associated with a known compound that exists in a database. The measurement element 86 may be additionally configured to provide a variation in temperature to the compound during system operation. The analysis element 88 may be configured and operable to construct a curve from peaks of at least one of a transmitted spectra, a reflected spectra and an absorbed spectra to develop a wideband curve or profile over at least one of the microwave and millimeter bands. The analysis element 88 can be further configured to use at least one additional comparison of at least one spectral span from 1 KHz to 1 GHz.

The analysis element 88 can be configured to execute or process at least one of an Fast Fourier transform (FFT) algorithm or a Goertzel algorithm. The apparatus 80 can be configured detect a chemical composition for at least one of determining clothing content for manufacturing quality control, determining a remaining useful lifetime of clothing comprising preselected chemical property or properties and determining exposure resistance to hazardous chemicals.

The measuring element 86 and analysis element 88 can be combined into a single element, for example such as the above signal processing member 30.

An exemplary method for determining a presence and/or concentration of a compound 2 can comprise emitting, with an antenna 26, electromagnetic energy in a direction of the compound, receiving, with the antenna 26, reflected energy from the compound 2, and determining, with a signal processing member 30, based on an amount of the reflected energy, the concentration of the compound. Measuring amount of the reflected energy may comprise generating a curve based on an absorption coefficient of the compound 2. Measuring amount of the reflected energy may comprise selecting frequencies at which, upon absorption thereof, the compound undergoes state changes. Measuring amount of the reflected energy may comprise constructing a curve based on frequency peaks. Measuring amount of the reflected energy may comprise comparing phases at each frequency. Measuring amount of the reflected energy may comprise comparing phases between at least two frequencies.

An exemplary method for determining a presence and/or concentration of a compound 2 can comprise emitting, with an antenna 26, electromagnetic energy in a direction of the compound, receiving, with a receiving element, electromagnetic energy spectra reflected from the compound 2, receiving, at another receiving element, electromagnetic energy transmitted through the compound, and determining, with a signal processing member 30, based on amount(s) of the reflected energy and transmitted energy, the concentration of the compound. Measuring amount(s) of the reflected energy may comprise generating a curve based on an absorption coefficient of the compound 2. Measuring amount(s) of the reflected energy and transmitted energy may comprise selecting frequencies at which, upon absorption thereof, the compound undergoes state changes. Measuring amount(s) of the reflected energy and transmitted energy may comprise constructing a curve based on frequency peaks. Measuring amount(s) of the reflected energy and transmitted energy may comprise comparing phases at each frequency. Measuring amount(s) of the reflected energy and transmitted energy may comprise comparing phases between at least two frequencies.

In either of the above exemplary methods, the electromagnetic energy may be transmitted at one frequency within each of three frequency ranges: in a range from about 1 MHz to 1 about GHz, in a range from about 1 GHZ to about 10 GHZ, in a range from about 10 GHz to about 100 GHz and in a range from about 100 GHz to about 300 GHz.

In either of the above exemplary methods, the electromagnetic energy may be transmitted at two or more frequency in each of the following ranges: from about 1 MHz to 1 about GHz, from about 1 GHZ to about 10 GHZ, from about 10 GHz to about 100 GHz and from about 100 GHz to about 300 GHz.

In an examplary embodiment, both the apparatus and method allow untrained or minimally trained personnel to successfully utilize the technology for in-situ testing of the compound in the field so as to determine a presence and/or a concentration thereof.

The user may test for permethrin at a single location of the article of closing or may test at more than one location. If the user tests at more than one location, the user may make a decision based on the lowest measured concentration of the compound.

Figure 7:
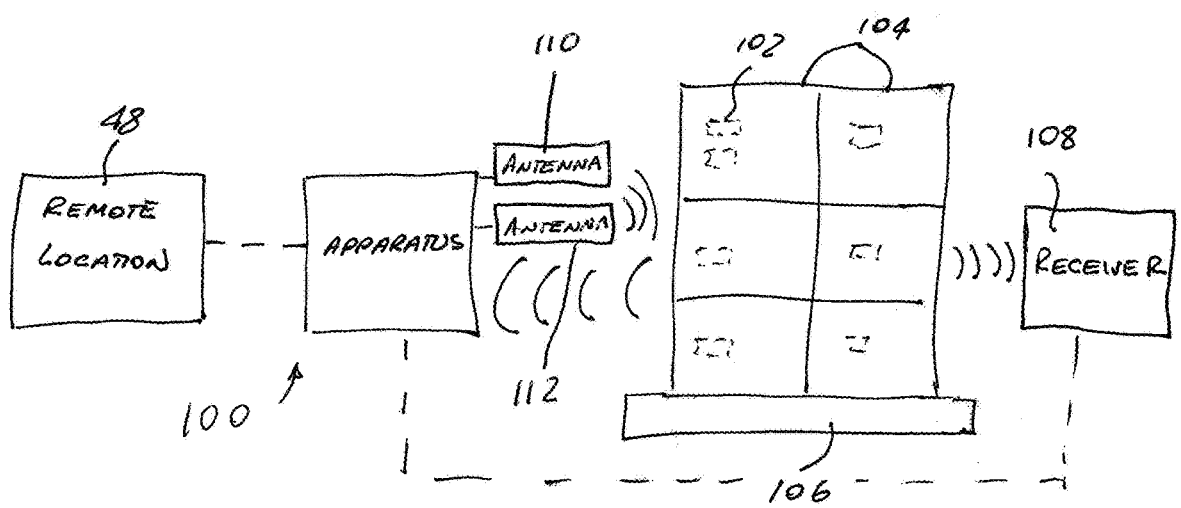
FIG. 7 illustrates a bloc diagram of an apparatus of another exemplary embodiment configured to detect a presence and/or a concentration of a chemical compound.

Either when the handheld device of FIGS. 1A, 1B and 1C is used or when the apparatus is provided as a benchtop apparatus, for example such as apparatus 80 or fixed device of FIG. 7, the compound 2 or the medium containing the compound 2 and the antenna 26 are positioned in a proximity to each other if not in a direct abutting contact with each other.

The feasibility of detecting permethrin and determining its concentration in articles of clothing using microwave absorption measurements has been demonstrated through experimentation. Clothing samples with varying permethrin levels were characterized by the above described apparatus to establish the correlative relationship between microwave absorption rates and permethrin concentration.

For testing on treated clothing articles, probes were connected to a network analyzer to generate microwave energy and receive attenuated signals. A frequency sweep was performed around permethrin's microwave absorption frequencies. Scattering parameters (Reflection—$S_{11}$ and Transmission—$S_{21}$) were measured at each frequency and saved to file. Tests were performed on each coupon no less than 100 times to establish statistical confidence in measurement results.

The performance and effectiveness of the above disclosed apparatus(es) and method(s) have been then verified by independently testing clothing samples with known concentrations of permethrin. Small test coupons (approximately 3"×3") were prepared by treating test coupons of clothing fabric to 0.142 mg/cm² concentration. Laundering cycles were then applied to reduce concentration to the desired level. Samples with known concentration were tested, with the described correlative function applied to measure the permethrin concentration in each sample. Results were compared against known values to validate the accuracy of the developed test methodology.

Statistics for the probability of detection (Pd) and false alarm rate (FAR) and test result accuracy provide firm evidence of the performance of the disclosed subject matter.

The following test results illustrate capability of the disclosed subject matter in detecting extremely low concentrations of permethrin:

A typical value of $I_o$-I for a nonpolar chemical species is approximately $2.15 \times 10^{-12}$ cm$^{-1}$ for a concentration of 0.01 mg/cm²;

A 1 mW (0 dBm) initial signal passing through 1 cm of fabric with 0.01 mg/cm² permethrin treatment thereby experiences signal loss by 2.15 pW (−86.67 dBm);

The microwave sensor 10 of the disclosed invention is sensitive to signals as low as −172 dBm;

Since attenuation constant scales linearly with concentration ($\gamma \propto N$), the concentration resulting in a reduction in signal strength by −172 dBm can be directly calculated;

A permethrin concentration of $2.9 \times 10^{-11}$ mg/cm² could theoretically be detected;

Given environmental noise and other obfuscating parameters, it is safe to assume that a signal strength of −140 dBm would be required for high statistical confidence;

With high statistical confidence, permethrin concentration as low as $46.4 \times 10^{-9}$ mg/cm² (46 pico-grams per square centimeter) is detectable using the disclosed invention.

Further, the following end results were achieved (derived) for a handheld permethrin detection device:

Sensitivity to permethrin concentration as low as 0.010 mg/cm²;

Operability under a wide range of temperature, moisture, and dust conditions (e.g. MIL-STD-810G);

Results in less than 5 minutes;

Use by an untrained operator;

Measurement configuration (single-sided or through-transmission);

SWaP requirements;

Antenna receptivity, bandwidth, and operational frequency range needed to target permethrin absorption of microwave energy;

RF sensor sensitivity requirement to detect permethrin concentrations of interest;

Software requirements for data throughput needed to support time requirements; and Result reporting requirements for intelligible reporting to untrained operators.

It must be further noted that this document incorporates by reference teachings of the following documents owned by the assignee of this application: U.S. Pat. No. 7,515,094 issued to Keller, III et al. on Apr. 7, 2009; U.S. Pat. No. 8,063,813, issued to Keller on Nov. 22, 2011; U.S. Pat. No. 8,643,539 issued to Paully et al. on Feb. 2, 2014; U.S. Pat. No. 9,059,189 issued to Keller et al. on Jun. 6, 2015; U.S. utility patent application Ser. No. 13/410,797 filed on Mar. 2, 2012, titled "System and Method for Physically Detecting Counterfeit Electronics" and now published as U.S. publication number 2012-0226463 A1 on Sep. 6, 2012; U.S. utility patent application Ser. No. 14/199,072 filed on Mar. 6, 2014 and titled Acoustic-RF Multi-Sensor Material Characterization System; and S. utility patent application Ser. No. 14/199,166 filed on Mar. 6, 2014 and titled Automated Sensor System for RF Shielding Characterization In another exemplary embodiment, the apparatus and/or method may be configured, based on the apparatuses and method(s) described above, to detect a presence and/or concentration of the compound being a pharmaceutical compound (product) 102. Such compound 102 may comprise one or more chemical species.

Now in a particular reference to FIG. 7, the apparatus 100 may be of any type described above. The pharmaceutical compound 102 can be disposed within boxes 104 that can be further positioned on a pellet or base 104. It is also contemplated that a receiving element (receiver) 108 may be provided as a standalone element being coupled, in either wireless or wired manner, to the apparatus 100. It is further contemplated herewithin that the apparatus 100 may be coupled, in either wireless or wired manner, to a remote location that can be the above described remote location 48.

In example, the apparatus 100 can employ a single antenna, for example such as the above described antennas 26 or 82. In another example, the apparatus 100 may comprise a pair of antennas 110 and 112 to provide for beam steering of the electromagnetic energy.

Sharply defined frequency peaks of electromagnetic energy spectra derived from molecular vibration frequencies of the molecules may be used to determine species (composition) of such compound. Using microwave energy at a relatively low frequency, below that of UV, visible light, and even infrared, causes the bonds to only rotate, not break. Microwave spectroscopy may have been previously ignored as the spectra are derived from the rotation of molecular bonds which typically create broadband peaks and not the sharp, clearly defined peaks resulting from vibration. The subject matter provides for using highly-specific and a nonlinear frequency dependence of a dielectric constant across microwave frequencies for solids, and in particular pharmaceutical compounds and binders to discriminate between batches of counterfeit and authentic products and also between batches of authentic products manufactured at different times.

Microwave (MW) spectroscopy in solids may be derived from the rotational spectra of molecules due to an interaction with microwaves. The range may be from about 0.3 GHz to about 3.0 GHz. Microwaves easily penetrate low dielectric constant materials such as oxides, ceramics, glass, and composite materials, even when they are several inches thick. The absorption of microwaves in solids may be based on the exposure frequency, it is not discrete nor quantum based, not using the mechanism of a direct absorption of a microwave photon, but the material reacts to a high frequency electric field, hence quantum-mechanics are not needed for modeling this phenomena, only simpler classical electromagnetic effects on materials.

MW spectroscopy can be used in non-metallic solids in general and specifically in drug components analysis, counterfeit vs. authentic drug analysis, for quality control of authentically manufactured pharmaceuticals, and analysis of variations within a batch or across batches. It can also be used for measurement and analysis of drug degradation due to aging, humidity exposure, or prolonged temperature excursions. It may be advantageous for any one of the following factors:

- non-invasive: transmitter and receiver elements can be placed around, adjacent to, or in the vicinity of pill containers or bulk boxes containing individual containers to be analyzed;
- non-destructive;
- can be used for solids, liquids, gases and suspensions: because microwave spectra result from the dielectric constant which is different for different types of material, a broad range of materials generally, and pharmaceuticals specifically can be tested;
- can be used for samples which have binders or coloration which absorb IR, visible, or UV spectra;
- capable of analyzing a bulk sample in one step, or multiple batches simultaneously: microwaves radiate though the entire sample from the transmitter (antenna 26);
- analysis of large sample volumes, microwave wavelengths can easily penetrate into distant depths of material batches, yet can be easily beam steered to focus on analyzing a specific region, and/or rastered to obtain a 2-D or 3-D profile of sample compositions.

It should be noted that microwave spectra result from two physical properties:

1. Dielectric Constant ($\in'$)

As a microwave passes through a sample an alternating polarization within the material is created. The sample stores some of the wave energy, and releases it back to the wave slowly, reducing the wave's velocity:

In electromagnetics, permittivity is one of the fundamental material parameters, which affects the propagation of Electric Fields. Permittivity is typically denoted by the symbol $\in$. The term $\in_0$ is the permittivity of Free Space, which is measured in Farads/meter. This is the permittivity of a vacuum (no atoms present). The term $\in_r$ is known as the relative permittivity or dielectric constant. The permittivity of a medium is expressed as the product of the dielectric constant and the free space permittivity:

$$\in = \in_r \in_0$$

The dielectric constant $\in_r$ is always greater than or equal to 1.0. Related to this are the following equations:

The dissipation factor is given by the equation:

$$\tan \delta = \in''/\in$$

where, $\in''$ indicates the efficiency of converting microwave energy to heat i.e., the dielectric loss. $\in$ is the measure of the ability to absorb microwave energy, i.e., the dielectric constant.

$$\in' = (V\text{VAC})^2/(V\text{MIX})^2$$

Thus samples with different dielectric constants constituent compositions can be distinguished typically at a given temperature.

2. Dielectric Loss ($\in''$)

This is absorption which reduces the magnitude of the wave. As molecules re-orientate in the electric field, friction causes energy to be lost, reducing the amplitude of the wave. Complex microwave spectra are created from the relaxation in liquids and solids. Therefore multivariate analysis is most effective to interpret the spectra. Due to the width breadth and low height of the peaks in the microwave region vs. the narrow peaks and high height in the IR, visible or UV, this capability is less sensitive than higher frequency spectroscopic methods but is by far better for analysis of large sample volumes.

Nuclear Magnetic Resonance (NMR) based microwave spectroscopy is an enhancement to non-NMR microwave spectroscopy, and is also envisioned herein in applications where additional information is merited to be extracted from the desired samples, or as an alternative means of characterizing counterfeit, aged, degraded non-metallic (substantially non-conductive) compounds. The NMR derived data comes at the additional equipment cost, weight and power usage however.

It is further contemplated herewithin that other spectroscopy means such as Dielectric Depolarization Spectroscopy can be used as a substitute or in addition to microwave spectroscopy as they are derived from similar physical phenomena.

In the dielectric losses described above, many materials also show the power absorption losses through electrical conduction under microwave irradiation. The dielectric constant may express these losses by using a separate conduction term. The dielectric losses of the majority of solids depend strongly on these conduction terms, and also are often affected by temperature. In the case of alumina, resistance decreases with temperature as electrons are promoted into the conduction band from the O(2p) valence band, increasing its dielectric constant.

If the dielectric properties and geometry of the inclusions are known, it is possible to arrive at expressions for the dielectric behavior of the bulk sample. The non-linear variation of this quantity implies that little can be predictively deduced by calculation without the dielectric properties of a heterogeneous material unless the shapes of the inclusions are known. Agreement of the theoretical models with real systems has been demonstrated by a variety of means. At higher concentrations, account must be made of interparticle electrostatic interactions and attempts to do this have shown reasonable agreement with models.

A consideration of the subject matter can be a relaxation frequency of the material. Low loss pharmaceutical materials have a poor electrothermal coupling capacity with microwave, thus requiring instruments of high sensitivity and low resolution bandwidth to resolve features with the necessary accuracy.

In addition to the dielectric losses describe above, many pharmaceutical materials may also show losses through conduction under microwave irradiation. The complex dielectric constant may be expressed to take account of these losses by including a separate conduction term.

Materials have different properties when exposed to microwaves, related to the extent of absorption of the microwaves. The amount of microwave energy absorbed is expressed by the following equation:

$$P = 2\pi f v^2 E0 Er \tan \delta$$

Where
P=the power density of the material=energy absorbed (W/m$^3$)
f=frequency (Hz)
v=electric field (V/m)
E0=dielectric permissivity of free space (8.85×10-12 F/m)
Er=dielectric constant of the material
tan δ=loss tangent Some materials, such as dielectric resonator materials generally and specifically ZrTi04, utilize electromagnetic resonance rather than electromechanical resonance as a loss mechanism. Thus, it can be important to note that not all microwave losses take place through the electric vector of the wave, the magnetic field vector can initiate energy transfer through magnetic resonance effects in which the unpaired electron spins precess about internal fields.

Material dielectric properties of pharmaceuticals vary considerably with frequency. At microwave frequencies, linear relationships are present between cube-root functions of the dielectric parameters and the material density which enables dielectric properties of materials at various densities to be estimated by regression.

Electromagnetic energy (radiation) may be used to not only measure properties of a microwave absorbing compound but also change properties. Changes may include final pharmaceutical processing changes needed as a final manufacturing step to finish the compound or fine tune by increasing or decreasing by degradation the compound's overall strength or effectiveness, for example as a means to accurately deliver a predesignated concentration in a pill or volume of pharmaceutical powder. Other changes may include activating or deactivating heat sensitive markers on or within the pill or medication, said markers which may be chemical compounds inside the pill or medication or on the surface which change at least one of the coloration, appearance, odor, shape via melting or hardening, chemical properties, hardness, digestibility when exposed to acid, ph, solubility, flavor, or electromagnetic properties of the material, pill, compound or pharmaceutical. This apparatus thus may be used change, measure and/or change and measure the properties of the compounds.

Application of Peak Cleaning Techniques

Thermally stimulated current can be a versatile technique with variants that allow experimental deconvolution of complex spectra. Isolation of selected signals is possible by applying different peak cleaning techniques, some of which are supported by the software provided with the commercial instruments. One of the most common peak cleaning techniques (Creswell and Perlman 1970) consists of the following steps. The material is polarized by applying an electric field at a temperature above the peak maximum of the relaxation under study (at Tp>Tβ') for sufficient time, and quenching at a much lower temperature. The subsequent heating cycle is interrupted at a temperature between the apparent peak maxima (at TA: Tβ<TA<Tβ') in order to depolarize the low-temperature component only. Cooling the sample and reheating allows recording of the (nearly) pure high temperature signal. In a variant of this technique (Bucci et al. 1966) the specimen is polarized at a temperature Tp (Tβ≤Tp<Tβ') for a short time tp≈τβ(Tp)<<τβ'(Tp), so that dipoles contributing to the low-temperature signal are polarized at close to saturation, while dipoles of the higher temperature relaxation remain randomly oriented. Experiments performed with different Tp values provide information related to the character of the signals (e.g., the presence of single or distributed relaxations).

Multivariate curve resolution methods can be employed to recover the concentration profiles represented in the broad underlying microwave spectral features acquired. The primary goal of curve resolution algorithms is to ascertain the true value of concentration profile and pure component spectra.

An exemplary method to accomplish these estimates of the spectra and concentration profiles is evolving factor analysis which can be used in an alternating least squares step, iteratively refining them from an initial starting assumption point to eventually discriminate between separated underlying spectral constituent concentrations. Constraint propagation methods and considerations, such as kinetic constraints and non-negativity often aid optimization. Using weighted ridge regression with PLS (partial least squares), a discrimination formed from the observed microwave spectra can be generated.

Another exemplary method can use a generation and analysis of derivatives and deep derivatives of $2^{nd}$, $3^{rd}$, $4^{th}$ order to extract the constituent broad curves of separate pharmaceutically active compounds and inactive compounds (binders such as calcium carbonate, lactose, Maize starch, Avicel, Carbonate, Mannitol, Calcium Phosphate, or etc.) which combine to create the composite overall broad curve response of the material or pharmaceutical under test. Illustrated below is the combining of solids and their associated spectra, and the derivative operations needed to de-combine them into their constituent parts.

For the analysis of the spectral absorption, a standard Fast Fourier Transform (FFT) algorithm or a Geortzel algorithm can be utilized where the Geortzel algorithm being more efficient in some exemplary embodiments, than the standard FFT, for computing a N-point DFT.

In an exemplary embodiment the apparatus and/or method is configured to detect chemical composition in clothing for manufacturing quality control. In another exemplary embodiment, the apparatus is used for detection of chemical composition to determine remaining useful lifetime of clothing. In another exemplary embodiment, the apparatus and/or method is used for the detection the chemical composition of clothing to determine exposure to hazardous chemicals. In another exemplary embodiment, the apparatus and/or method is utilized for the detection of chemical weapon use. In another exemplar embodiment, the apparatus and/or method is used to determine the composition of drugs. In another exemplary embodiment the apparatus and/or method is used to determine if a drug is counterfeit or authentic. In another exemplary embodiment, the system is used to determine if an item whether it be a drug or piece of clothing or other was manufactured in the anticipated factory or if it was manufactured elsewhere.

In accordance with an exemplary embodiment, the processing member utilizes high order derivatives to extract constituent broad curves of separate pharmaceutically active compounds and inactive compounds and to recover concentration profiles represented in acquired underlying microwave spectral features.

In accordance with an exemplary embodiment, the apparatus is configured to analyze pharmaceuticals in pill containers with microwave spectroscopy to determine authenticity based on substantial similarity to known good reference pharmaceuticals in the containers.

In accordance with an exemplary embodiment, the apparatus is configured to analyze pharmaceuticals in pill containers in boxes with microwave spectroscopy to determine authenticity based on substantial similarity to known good reference pharmaceuticals in the containers. The boxes may be disposed on pallets.

In accordance with an exemplary embodiment, the apparatus is configured to analyze pharmaceuticals in pill containers in boxes on pallets with microwave spectroscopy to determine a degradation based on a comparison to known good reference pharmaceuticals in the containers.

In accordance with one exemplary embodiment, the apparatus is configured to analyze pharmaceuticals in pill containers in boxes on pallets with microwave spectroscopy to determine tampering occurrence based on substantial similarity to known good reference pharmaceuticals in the containers.

In accordance with an exemplary embodiment, the apparatus and/or method may employ beam steering. In one example, beam steering may be employed to analyze a region of pharmaceuticals. In another example, beam steering may be employed to generate a profile of authentic versus inauthentic pharmaceuticals. In another example, beam steering may be employed to generate a profile of degraded vs non-degraded pharmaceuticals. In another example, beam steering may be employed to generate a profile of tampered vs non-tampered pharmaceuticals. In another example, beam steering may be employed to generate a tomographic profile of pharmaceuticals microwave absorption.

In accordance with an exemplary embodiment, the known good reference pharmaceuticals may be examined using microwave radiation in an anechoic chamber for later comparison with pharmaceuticals to be tested.

In accordance with an exemplary embodiment, microwave radiation may not only be used to profile pharmaceutical microwave absorption characteristics, but used to further heat the compound under test to observe a characteristic change of microwave absorption at at least one of a new temperature or a change of temperature.

In accordance with an exemplary embodiment, microwave radiation may be used to generate characteristic curves of microwave absorption vs. temperature of known authentic, non-degraded, non-tampered materials to be compared with questionable materials in the same manner.

According to an exemplary embodiment, a compound detection sensor (apparatus) comprises a housing defining a hollow interior and one end being configured for positioning adjacent or on a surface of a fabric material containing the compound; a microwave power supply disposed within the hollow interior; an antenna disposed within the hollow interior adjacent the one end of the housing, the antenna electrically coupled to the microwave power supply, the antenna adapted, during operation of the apparatus, to emit energy during use of the apparatus, the antenna further adapted to receive an unabsorbed energy from the material and generate a signal defining the unabsorbed energy; a signal processing member disposed within the housing and coupled to each of the microwave power supply and the antenna, the signal processing components configured, during operation of the apparatus, to process the signal and determine a concentration and/or a presence of the compound on/in the fabric material; and a reporting member coupled to the signal processing member the reporting component configured, during operation of the apparatus, to communicate the concentration and/or presence of the compound on/in the fabric material.

According to an exemplary embodiment, a compound detection sensor (apparatus) comprises a housing defining a hollow interior and one end being configured for positioning adjacent or on a surface of a fabric material containing the compound; a microwave power supply disposed within the hollow interior; an antenna disposed within the hollow interior adjacent the one end of the housing, the antenna electrically coupled to the microwave power supply, the antenna adapted, during operation of the apparatus, to emit energy during use of the apparatus, the antenna further adapted to receive an unabsorbed energy from the material and generate a signal defining the unabsorbed energy; a signal processing member disposed within the housing and coupled to each of the power supply and the antenna, the signal processing components configured, during operation of the apparatus, to process the signal and determine a concentration and/or a presence of the compound on/in the fabric material, the signal processing member comprising an LNA coupled to the antenna, a filter coupled to an output from the LNA, a processing member coupled to the filter and comprising one or more processors and a computer program stored in memory and; and a reporting member coupled to the signal processing member the reporting component configured to communicate the concentration and/or presence of the compound on/in the fabric material, the reporting member comprising a display and a pair of LEDs.

According to an exemplary embodiment, a compound detection sensor (apparatus) comprises a housing defining a hollow interior and one end being configured for positioning adjacent or on a surface of a fabric material containing the compound; a microwave power supply disposed within the hollow interior; an antenna disposed within the hollow interior adjacent the one end of the housing, the antenna electrically coupled to the microwave power supply, the antenna adapted, during operation of the apparatus, to emit energy during use of the apparatus, the antenna further adapted to receive an unabsorbed energy from the material and generate a signal defining the unabsorbed energy; a signal processing member disposed within the housing and coupled to each of the power supply and the antenna, the signal processing components configured, during operation of the apparatus, to process the signal and determine a concentration and/or a presence of the compound on/in the fabric material; a reporting member coupled to the signal processing member the reporting component configured, during operation of the apparatus, to communicate the concentration and/or presence of the compound on/in the fabric material; a transceiver couplet to the signal processing member; and a remote location coupled to the signal processing member through the transceiver.

According to an embodiment, a compound detection sensor (apparatus) comprises a microwave power supply; an antenna electrically coupled to the microwave power supply, the antenna adapted, during operation of the apparatus, to emit energy during use of the apparatus, the antenna further adapted to receive an unabsorbed energy from the material and generate a signal defining the unabsorbed energy; a signal processing member coupled to each of the microwave power supply and the antenna, the signal processing components configured, during operation of the apparatus, to process the signal and determine a concentration and/or a presence of the compound on/in the fabric material; and a reporting member coupled to the signal processing member the reporting component configured, during operation of the apparatus, to communicate the concentration and/or presence of the compound on/in the fabric material.

According to an exemplary embodiment, a compound detection apparatus comprises a DC power supply, a microwave power supply; an antenna electrically coupled to the microwave power supply, the antenna adapted, during operation of the apparatus, to emit energy during use of the apparatus, the antenna further adapted to receive an unabsorbed energy from the material and generate a signal defining the unabsorbed energy; a signal processing member coupled to each of the microwave power supply and the antenna, the signal processing components configured, during operation of the apparatus, to process the signal and determine a concentration and/or a presence of the compound on/in the fabric material; and a reporting member coupled to the signal processing member the reporting component configured, during operation of the apparatus, to communicate the concentration and/or presence of the compound on/in the fabric material.

According to an exemplary embodiment, a compound detection apparatus comprises a microwave power supply disposed; an antenna electrically coupled to the microwave power supply and adapted to emit modulated energy during use of the apparatus; one or more receivers adapted to receive an unabsorbed and/or transmitted energy from the material and generate a respective signal defining the unabsorbed energy and/or transmitted energy; a signal processing member disposed within the housing and coupled to each of the power supply and the antenna, the signal processing components configured to process the signal and determine a concentration and/or a presence of the compound on/in the fabric material; and a reporting member coupled to the signal processing member the reporting component configured to communicate the concentration and/or presence of the compound on/in the fabric material.

In one example, the compound can be a liquid at room temperature. In another example, the compound can be an organic chemical compound. The organic chemical compound may have absorption spectra resulting in energy loss at selected characteristic frequencies. In another example, the compound can be a organophosphorus compound. In another example, the compound can be Permethrin. In another example, the compound can be present in a gaseous form. In another example, the compound can be present in a solid form.

According to one example, the apparatus can be configured as a handheld device comprising a hollow housing and wherein the reporting member is accessible from an exterior surface of the housing. The handheld device may weigh less than 3 lbs. The handheld housing may completely covers a region of the fabric material on one or both side of thereof. The housing may be configured to substantially shield by a reduction of 100 times or more the fabric material and the antenna from sources of external radiation being at least one of RF radiation, microwave radiation, millimeter-wave radiation, Terahertz wave radiation, infrared radiation, visible light radiation ultraviolet radiation and x-ray radiation.

According to another example, the apparatus can be configured as a benchtop device. According to one example, the apparatus can be configured as a stationary device. The stationary device may have one or more receivers. One receiver may be disposed remotely from and coupled to the device.

According to one exemplary embodiment, the fabric material is any one of wearable, to be worn and previously worn.

According to one exemplary embodiment, the antenna can be configured to emit the energy at frequencies of at least one of RF radiation, microwave radiation, millimeter-wave radiation, Terahertz wave radiation, infrared radiation, visible light radiation ultraviolet radiation and x-ray radiation.

According to one exemplary embodiment, an illumination receiver element can be provided and configured to detect electromagnetic energy radiation at frequencies of at least one of RF radiation, microwave radiation, millimeter-wave radiation, Terahertz wave radiation, infrared radiation, visible light radiation ultraviolet radiation and x-ray radiation.

According to another exemplary embodiment, the reporting member is configured to generate at least one of visual, audio, and tactile signaling elements indicating a threshold degree of the compound concentration in the fabric material.

According to an exemplary embodiment, the antenna can emit electromagnetic energy (radiation) at pre-chosen frequencies within about 30 Mhz to about 30 Ghz range, corresponding to absorption frequencies associated with the compound.

According to an exemplary embodiment, the signal processing member is an electromagnetic receiver that translates electromagnetic energy frequencies received into at least one of digital or analog translated representations.

According to an exemplary embodiment, the signal processing member executes an FFT transform.

According to one exemplary embodiment, the signal processing member comprises a Low Noise Amplifier to increase power level of the signal from the antenna.

According to one exemplary embodiment, the signal processing member comprises a hardware or software tuner to tune the transmitted energy to predesignated absorption frequencies associated with the compound.

According to one exemplary embodiment, the signal processing member comprises a set of hardware or software bandpass or band reject filters tuned to the specifically predesignated absorption frequencies associated with the compound.

According to one exemplary embodiment, the reporting member can report a threshold of level of absorption of one or more absorption frequencies of the compound based on matching to levels represented in a predesignated mask of absorption frequencies for the compound.

According to one exemplary embodiment, acquired absorption spectra resulting in energy loss can be defined by a broad curve of loss versus frequencies.

In one example, the processing member can execute multivariate curve resolution methods to recover concentration profiles represented in an acquired underlying microwave spectral features.

In one example, the processing member can utilize evolving factor analysis to recover concentration profiles represented in the acquired underlying microwave spectral features.

In one example, the processing member can utilize constraint propagation to recover concentration profiles representing the acquired underlying microwave spectral features.

In one example, the processing member can utilize high order derivatives to extract constituent broad curves of separate pharmaceutically active compounds and inactive compounds and to recover concentration profiles represented in acquired underlying microwave spectral features.

According to an exemplary embodiment, the apparatus can be configured to analyze pharmaceuticals in pill containers with microwave spectroscopy to determine authenticity based on substantial similarity to known good reference pharmaceuticals in the containers.

According to an exemplary embodiment, the apparatus can be configured to analyze pharmaceuticals in pill containers in boxes with microwave spectroscopy to determine authenticity based on substantial similarity to known good reference pharmaceuticals in the containers.

According to an exemplary embodiment, the boxes can be disposed on pallets. A standalone receiver may be also provided to receive radiation passing through boxes on pallet.

According to an exemplary embodiment, the apparatus can be configured to analyze pharmaceuticals in pill containers in boxes on pallets with microwave spectroscopy to determine a degradation based on a comparison to known good reference pharmaceuticals in the containers.

According to an exemplary embodiment, the apparatus can be configured to analyze pharmaceuticals in pill containers in boxes on pallets with microwave spectroscopy to determine tampering occurrence based on substantial similarity to known good reference pharmaceuticals in the containers.

According to an exemplary embodiment, beam steering can be employed to analyze a region of pharmaceuticals. In one example, beam steering can be employed to generate a profile of authentic versus inauthentic pharmaceuticals. In another example, beam steering can be employed to generate a profile of degraded vs non-degraded pharmaceuticals. In another example, beam steering can be employed to generate a profile of tampered vs non-tampered pharmaceuticals. In another example, beam steering can be employed to generate a tomographic profile of pharmaceuticals microwave absorption.

According to an exemplary embodiment, the known good reference pharmaceuticals can be examined using microwave radiation in an anechoic chamber for later comparison with pharmaceuticals to be tested.

According to an exemplary embodiment, microwave radiation can be not only measured to profile pharmaceutical microwave absorption characteristics, but used to further heat the substance under test to observe a characteristic change of microwave absorption at at least one of a new temperature or a change of temperature.

According to an exemplary embodiment, microwave radiation can be used to generate characteristic curves of microwave absorption versus temperature of known authentic, non-degraded, non-tampered materials to be compared with questionable materials in the same manner.

According to an exemplary embodiment, a compound detection system comprises an illumination element being at least one of RF, microwave and millimeter wave illumination transmission type, configured and operable to illuminate, with electromagnetic energy, a compound under a test and/or a detection; a receiver element configured to receive a spectra of the electromagnetic energy that is transmitted through a medium that contains the compound under the test and/or the detection;

a receiver element configured to receive a spectra of electromagnetic energy that is reflected from the medium that contains the compound under the test and/or the detection; a measurement element that is connected to at least one of the receiver element configured to receive the spectra of electromagnetic energy that is reflected from the medium and the receiver element configured to receive the spectra of electromagnetic energy that is reflected from the medium, the measurement element configured to determine a value or amount of reflected electromagnetic energy and/or absorbed electromagnetic energy; and an analysis element that analyzes information collected by the measurement element and defines chemical specie(s) within the compound.

In one example, the illumination element is operable to transmit the electromagnetic energy at at least one frequency.

In another example, the illumination element is operable to transmit the electromagnetic energy at least one frequency being in a range from about 1 MHz to 1 about GHz, in a range from about 1 GHZ to about 10 GHZ; in a range from about 10 GHz to about 100 GHz and in a range from about 100 GHz to about 300 GHz.

In another example, the illumination element can be operable to transmit one or more frequency in each of a frequency range from about 1 MHz to about 1 GHz, a frequency range from about 1 GHZ to about 10 GHZ, a frequency range from about 10 GHz to about 100 GHz and a frequency range from about 100 GHz to about 300 GHz can be utilized simultaneously to differentiate the chemical make-up of a compound.

In one example, the illumination element can be operable to transmit the electromagnetic energy at one or more frequencies and wherein at least one of the one or more frequencies can be modulated to determine chemical composition of the compound.

In another example, the analysis element can compare phases of at least one of the reflected and transmitted electromagnetic energy.

In one example, the analysis element can compare phases of at least two frequencies.

In one example, the analysis element can compare phases of at least one of the reflected and transmitted electromagnetic energy over at least two different frequencies.

In one example, absorption spectra in the compound can result in the electromagnetic energy loss at at least two characteristic frequencies.

In another example, the measurement element can comprise a hardware or software tuner to tune the illumination element to specifically predesignated absorption frequencies associated with the compound.

In another example, the measurement element can comprise algorithms to reactively at least one of tune to specifically predesignated absorption frequencies and provide a specific modulation parameter associated with a known compound that can be stored in a database.

In another example, the measurement element can be additionally configured to provide a variation in temperature to the compound during system operation.

In another example, the analysis element can be configured and operable to construct a curve from peaks of at least one of transmitted spectra, reflected spectra and absorbed spectra to develop a wideband profile over at least one of the microwave and millimeter bands.

In another example, the analysis element can be further configured to process at least one additional comparison of at least one spectral span from 1 KHz to 1 GHz.

In another example, the analysis element can be configured to execute or process at least one of an Fast Fourier transform (FFT) algorithm or a Goertzel algorithm.

In another example, the apparatus can be configured to detect a chemical composition for at least one of determining clothing content for manufacturing quality control, determining a remaining useful lifetime of clothing comprising preselected chemical property or properties and determining exposure resistance to hazardous chemicals.

In another example, the apparatus can measure the microwave radiation to profile at least one of microwave absorption characteristics of a pharmaceutical compound being a solid form and heat the at least one of pharmaceutical compound to change property or properties thereof.

According to an exemplary embodiment, a method for determining a concentration of a compound can comprise sweeping, with a frequency generator coupled to an antenna, the compound with an electromagnetic energy in a range of frequencies; measuring scattering parameters at each frequency within the range of frequencies; and determining, based on the scattering parameters, the concentration of the compound.

In an example, measuring scattering parameters can comprise generating a response curve based on an absorption coefficient of the compound. In an example, measuring scattering parameters can comprise selecting frequencies at which, upon absorption thereof, the compound undergoes state changes. In an example, measuring scattering parameters can comprise constructing a curve based on frequency peaks. In an example, measuring scattering parameters can comprise comparing phases at each frequency. In an example, measuring scattering parameters can comprise comparing phases between at least two frequencies.

According to an exemplary embodiment, a method for determining a concentration of a compound can comprise emitting, with an antenna, electromagnetic energy in a direction of the compound; receiving, with the antenna, reflected energy from the compound; and determining, based on an amount of the reflected energy, the concentration of the compound.

According to an exemplary embodiment, a method for determining a concentration of a compound can comprise emitting, with an antenna, electromagnetic energy in a direction of the compound; receiving, with the antenna, energy reflected from the compound; receiving, at another antenna, energy transmitted through the compound; and determining, based on amount(s) of the reflected energy and transmitted energy, the concentration of the compound According to an exemplary embodiment, the processing member may be implemented as a computer program executed by a computer. For example, the processing member may take a form of a computer program containing one or more sequences of machine-readable instructions describing a method as disclosed above, or a data storage medium (e.g., semiconductor memory, magnetic or optical disk) having such computer program stored therein.

Computer program code for carrying out operations for aspects of various embodiments may be written in any combination of one or more programming languages, including an object oriented programming language, such as Java, Smalltalk, C++, or the like, and conventional procedural programming languages, such as the "C" programming language or similar programming languages. In accordance with various implementations, the program code may execute entirely in the apparatus, partly on in the apparatus, as a stand-alone software package, partly in the apparatus and partly on a remote computer or entirely on the remote computer or server. In the latter scenario, the remote computer may be connected to the processing member in the apparatus through any type of wireless or non-wireless network, including a local area network (LAN) or a wide area network (WAN), or the connection may be made to an external computer (for example, through the Internet using an Internet Service Provider).

Any combination of one or more computer readable storage medium(s) may be utilized. A computer readable storage medium may be embodied as, for example, an electronic, magnetic, optical, electromagnetic, infrared, or semiconductor system, apparatus, or device, or other like storage devices known to those of ordinary skill in the art, or any suitable combination of computer readable storage mediums described herein. In the context of this document, a computer readable storage medium may be any tangible medium that can contain, or store a program and/or data for use by or in connection with an instruction execution system, apparatus, or device.

According to a further exemplary embodiment, the computer may comprise a communication module comprising the receiving and/or transmitting members.

Persons of ordinary skill in the art may appreciate that, in combination with the examples described in the embodiments herein, units and algorithm steps can be implemented by electronic hardware, computer software, or a combination thereof. In order to clearly describe the interchangeability between the hardware and the software, compositions and steps of every embodiment have been generally described according to functions in the foregoing description. Whether these functions are performed using hardware or software depends on particular applications and design constraints of the technical solutions.

A person skilled in the art may use different methods to implement the described functions for each specific application. However, such implementation should not be considered as beyond the scope of the present invention.

Figure 6:
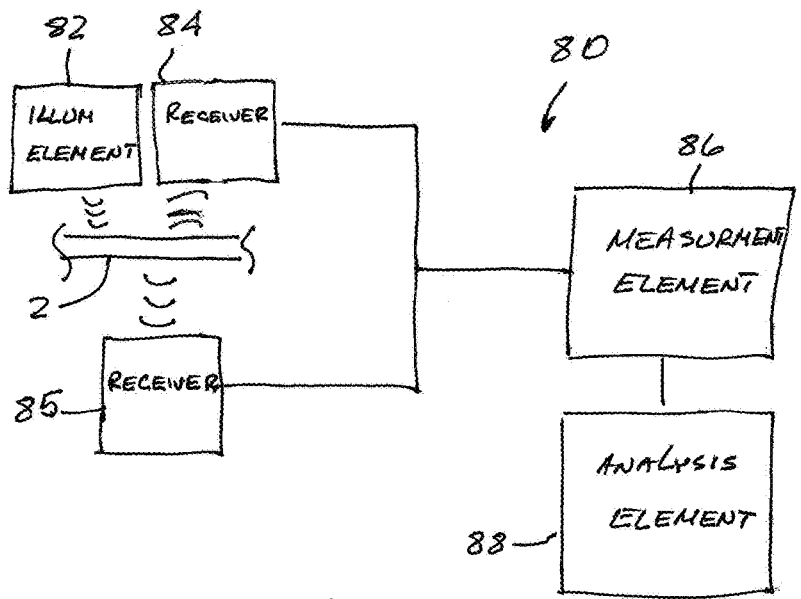
FIG. 6 illustrates a bloc diagram of an apparatus of another exemplary embodiment configured to detect a presence and/or a concentration of a chemical compound.

The chosen exemplary embodiments of the claimed invention have been described and illustrated for practical purposes so as to enable any person skilled in the art to which it pertains to make and use the same. It is therefore intended that all matters in the foregoing description and shown in the accompanying drawings be interpreted as illustrative and not in a limiting sense. It will be understood that variations, modifications, equivalents and substitutions for components of the specifically described exemplary embodiments of the invention may be made by those skilled in the art without departing from the spirit and scope of the invention as set forth in the appended claims. It is to be further understood that various features may be interchanged between the above described apparatuses and methods. For example, steps performed for detecting chemical compound on an article of clothing may be used to detect pharmaceutical compound stored in a box and vice-versa. The reporting member 50 may be employed within the apparatus 100 of FIG. 7 and the remote location 48 may be employed with the apparatus 80 of FIG. 6.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the term "coupled" and/or "connected" includes direct and indirect connections. Moreover, where first and second devices are coupled, intervening devices including active devices may be located there between.

Any element in a claim that does not explicitly state "means for" performing a specified function, or "step for" performing a specified function, is not to be interpreted as a "means" or "step" clause as specified in 35 U.S.C. § 112, ¶6. In particular, any use of "step of" in the claims is not intended to invoke the provision of 35 U.S.C. § 112, ¶6.

Unless otherwise indicated, all numbers expressing quantities of elements, optical characteristic properties, and so forth used in the specification and claims are to be understood as being modified in all instances by the term "about." Accordingly, unless indicated to the contrary, the numerical parameters set forth in the preceding specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible.

Any numerical value, however, inherently contains certain errors necessarily resulting from the standard deviations found in their respective testing measurements.

The recitation of numerical ranges by endpoints includes all numbers subsumed within that range (e.g. 1 to 5 includes 1, 1.5, 2, 2.75, 3, 3.80, 4, and 5).

Anywhere the term "comprising" is used, embodiments and components "consisting essentially of" and "consisting of" are expressly disclosed and described herein."

Furthermore, the Abstract is not intended to be limiting as to the scope of the claimed invention and is for the purpose of quickly determining the nature of the claimed invention.

What is claimed is:

1. A compound detection apparatus, comprising:
   a handheld housing defining a hollow interior and one end being configured for positioning adjacent to or on a surface of a fabric material containing said compound;
   a microwave power supply disposed within said hollow interior;
   an antenna disposed within said hollow interior adjacent said one end of said housing, said antenna electrically coupled to said microwave power supply, said antenna adapted, during operation of said apparatus, to emit electromagnetic energy, receive a spectra of electromagnetic energy reflected from the material, and generate a signal defining said reflected electromagnetic energy;
   a signal processing member disposed within said housing and coupled to each of said microwave power supply and said antenna, said signal processing member configured, during said operation of said apparatus, to measure scattering parameters at each frequency within said spectra represented by said signal and determine, based on said scattering parameters, a concentration and/or a presence of the compound on/in the fabric material; and
   a reporting member coupled to said signal processing member, said reporting component configured, during said operation of said apparatus, to communicate said concentration and/or presence of the compound on/in the fabric material.

2. The apparatus of claim 1, wherein the compound is any one of a liquid at room temperature, an organic chemical compound, a organophosphorus compound, and a Permethrin.

3. The apparatus of claim 1, wherein the compound is an organic chemical compound that has absorption spectra resulting in energy loss at selected characteristic frequencies.

4. The apparatus of claim 1, wherein said one end comprises a faceplate having said antenna embedded therewithin.

5. The apparatus of claim 1, wherein said housing is configured to substantially shield by a reduction of 100 times or more the fabric material and said antenna from sources of external radiation being at least one of RF radiation, microwave radiation, millimeter-wave radiation, Terahertz wave radiation, infrared radiation, visible light radiation ultraviolet radiation and x-ray radiation.

6. The apparatus of claim 1, wherein said reporting member is configured to generate at least one of visual, audio, and tactile signaling elements indicating a threshold degree of said compound concentration in the fabric material.

7. The apparatus of claim 1, wherein said reporting member comprises a display screen and a pair of light emitting diodes.

8. The apparatus of claim 1, wherein said antenna emits energy at pre-chosen frequencies within about 30 Mhz to about 30 Ghz range, corresponding to absorption frequencies associated with the compound.

9. The apparatus of claim 1, wherein said signal processing member is an electromagnetic receiver that translates received electromagnetic energy frequencies into at least one of digital and analog translated representations.

10. The apparatus of claim 1, wherein said signal processing member comprises a Low Noise Amplifier (LNA) and a set of hardware or software bandpass or band reject filters tuned to predesignated absorption frequencies associated with the compound.

11. The apparatus of claim 1, wherein said signal processing member comprises one or more processors and a non-transitory tangible computer readable medium and/or tangible computational medium comprising algorithms and/or executable instructions (computer program code), that cause the one or more processors to process said signal defining the reflected energy.

12. The apparatus of claim 11, wherein said processing member executes multivariate curve resolution methods to recover concentration profiles represented in an acquired underlying microwave spectral features.

13. The apparatus of claim 12, wherein said processing member utilizes evolving factor analysis to recover concentration profiles represented in said acquired underlying microwave spectral features.

14. The apparatus of claim 11, wherein said signal processing member executes a Fast Fourier Transform (FFT).

15. A compound detection system comprising:
    an illumination element being at least one of RF, microwave and millimeter wave illumination transmission type, configured and operable to sweep a compound under a test and/or a detection by way of illuminating the compound with an electromagnetic energy in a range of frequencies;

a first receiver element configured to receive a first spectra of the electromagnetic energy that is transmitted through a medium that contains the compound under the test and/or the detection;

a second receiver element configured to receive a second spectra of electromagnetic energy that is reflected from the medium that contains the compound under the test and/or the detection;

a measurement element that is connected to at least one of the first receiver element and second receiver element, said measurement element configured to measure scattering parameters at each frequency within each of said first spectra and said second spectra of electromagnetic energy and to determine a value or amount of at least one of reflected electromagnetic energy and absorbed electromagnetic energy; and an analysis element that analyzes information collected by said measurement element and defines, based on said scattering parameters, chemical specie(s) within said compound.

16. The apparatus of claim 15, wherein said illumination element is operable to transmit said electromagnetic energy at least one frequency being in a range from about 1 MHz to 1 about GHz, in a range from about 1 GHZ to about 10 GHZ; in a range from about 10 GHz to about 100 GHz and in a range from about 100 GHz to about 300 GHz.

17. The apparatus of claim 15, wherein said measurement element comprises a hardware or a software tuner to tune said illumination element to specifically predesignated absorption frequencies associated with said compound.

18. The method of claim 15, wherein measuring said scattering parameters comprises at least one of generating a curve based on an absorption coefficient of the compound, selecting frequencies at which, upon absorption thereof, the compound undergoes state changes, constructing a curve based on frequency peaks, comparing phases at each frequency, and comparing phases between at least two frequencies.

19. The method of claim 15, wherein method further comprises use of peak cleaning techniques.

20. The method of claim 15, further comprising calculating a loss tan δ based on attenuated energy at each frequency and identifying frequency or frequencies at which an energy state transition occurs.

21. A method for determining a concentration and/or a presence of a Permethrin on/in a fabric material, comprising:
providing a hand-held device comprising a housing with a hollow interior and a face plate at one end of said housing, an antenna disposed within said hollow interior adjacent to or being imbedded in said face plate, a frequency generator coupled to said antenna, and a signal processing member coupled to said antenna;
sweeping, with said frequency generator coupled to said antenna, said fabric material with an electromagnetic energy in a range of frequencies corresponding to absorption frequencies of said Permethrin;
measuring, with said signal processing member, scattering parameters at each frequency within said range of frequencies; and
determining, with said signal processing member, based on said scattering parameters, said concentration and/or said presence of said Permethrin.

22. The method of claim 21, wherein measuring scattering parameters comprises selecting frequencies of said electromagnetic energy at which, upon absorption thereof, said compound undergoes state changes.

23. The method of claim 21, wherein said device further comprises a reporting member configured to communicate the concentration and/or presence of said Permethrin.

24. The method of claim 21, wherein said reporting member comprises a display and a pair of light emitting diodes, said display and said pair of light emitting diodes viewable from an exterior surface of said housing.

* * * * *